United States Patent [19]

Novak

[11] 4,414,531
[45] Nov. 8, 1983

[54] PARTIAL PRESSURE OF OXYGEN SENSOR-I

[75] Inventor: Robert F. Novak, Farmington Hills, Mich.

[73] Assignee: Ford Motor Company, Dearborn, Mich.

[21] Appl. No.: 429,414

[22] Filed: Sep. 30, 1982

[51] Int. Cl.³ .............................................. H01L 7/00
[52] U.S. Cl. ................................... 338/34; 73/27 R; 422/98
[58] Field of Search ........................... 338/34, 28, 13; 73/27 R; 422/98

[56] References Cited

U.S. PATENT DOCUMENTS

| 4,001,758 | 1/1977 | Esper et al. ...................... 338/28 X |
| 4,193,965 | 3/1980 | Cullingford et al. ............ 73/27 R X |
| 4,243,968 | 1/1981 | Scott ..................................... 338/28 |
| 4,308,518 | 12/1981 | Hattori et al. .................. 73/27 R X |

Primary Examiner—C. L. Albritton
Attorney, Agent, or Firm—William E. Johnson; Olin B. Johnson

[57] ABSTRACT

A partial pressure of oxygen sensor which finds utility when inserted into an exhaust system of a hydrocarbon fuel burning device. The oxygen sensor includes a mounting body threaded on one end for securement to the exhaust system and having a conical configured bore extending along a central axis thereof and having its smaller end at the threaded end of the mounting body. An elongated heated sensing element is also provided which includes a ceramic support, a resistance heater element, and a titania dioxide sensor element bonded to a leading portion of the ceramic support. A plurality of electrically conductive paths are provided on the ceramic support for the elements contained thereon. An insulator body having a conical configuration sandwiches the heated sensing element therewithin. The insulator body is mounted in the conical configured bore of the mounting body in a manner that the heated sensing element projects a fixed distance beyond the threaded end of the mounting body. A protection device is provided over the leading portion of the heated sensing element. Electrical connections are made by means of electrical lead wires at the rear end of the mounting body to the circuit paths on the ceramic support. Further structure is provided for supporting and sealing the electrical lead wires in a manner that the electrical lead wires may be connected to a suitable connector, whereby the heated sensing element can be connected to a source of voltage and the titania dioxide sensing element to a sensing circuit.

3 Claims, 8 Drawing Figures

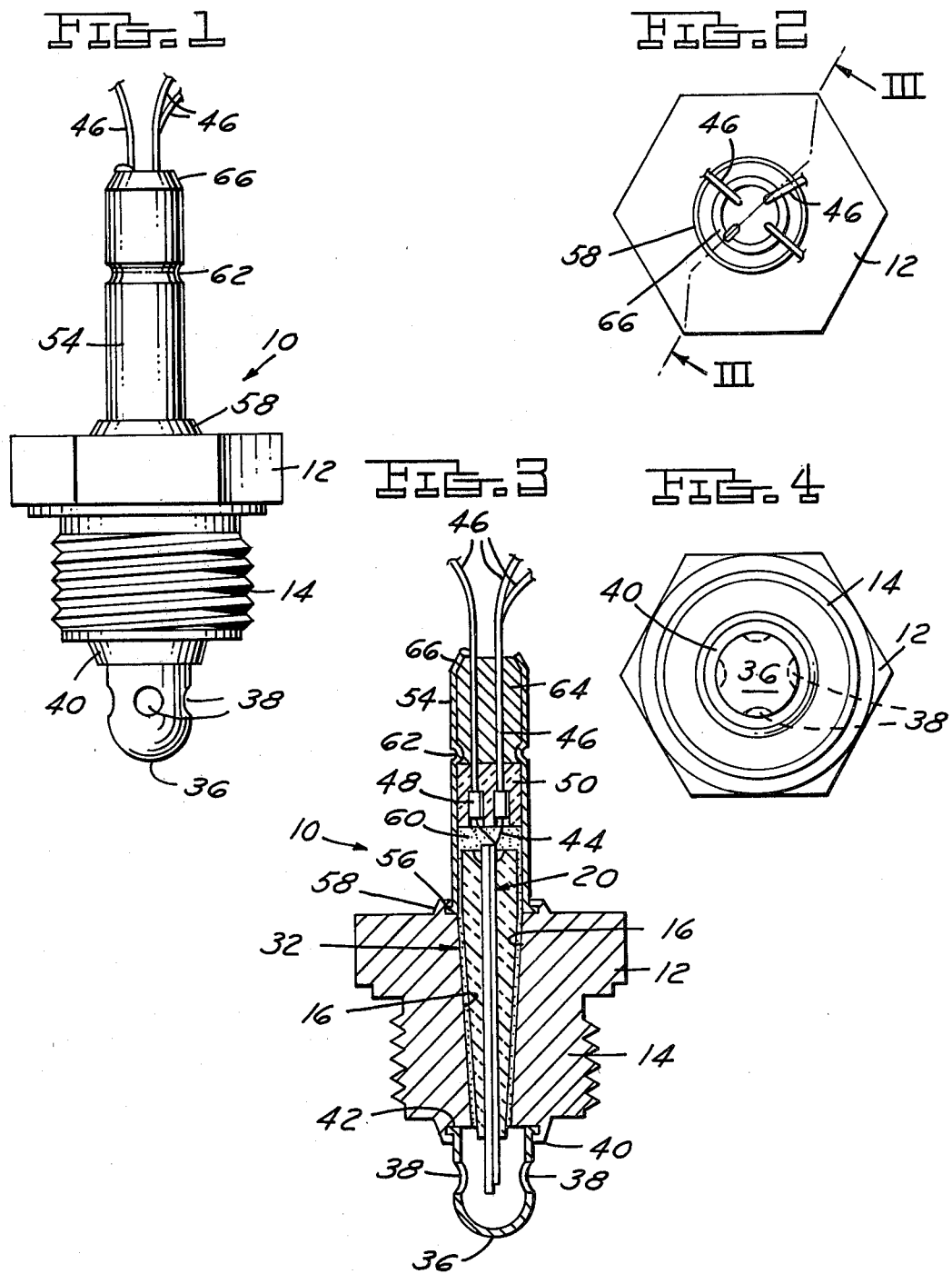

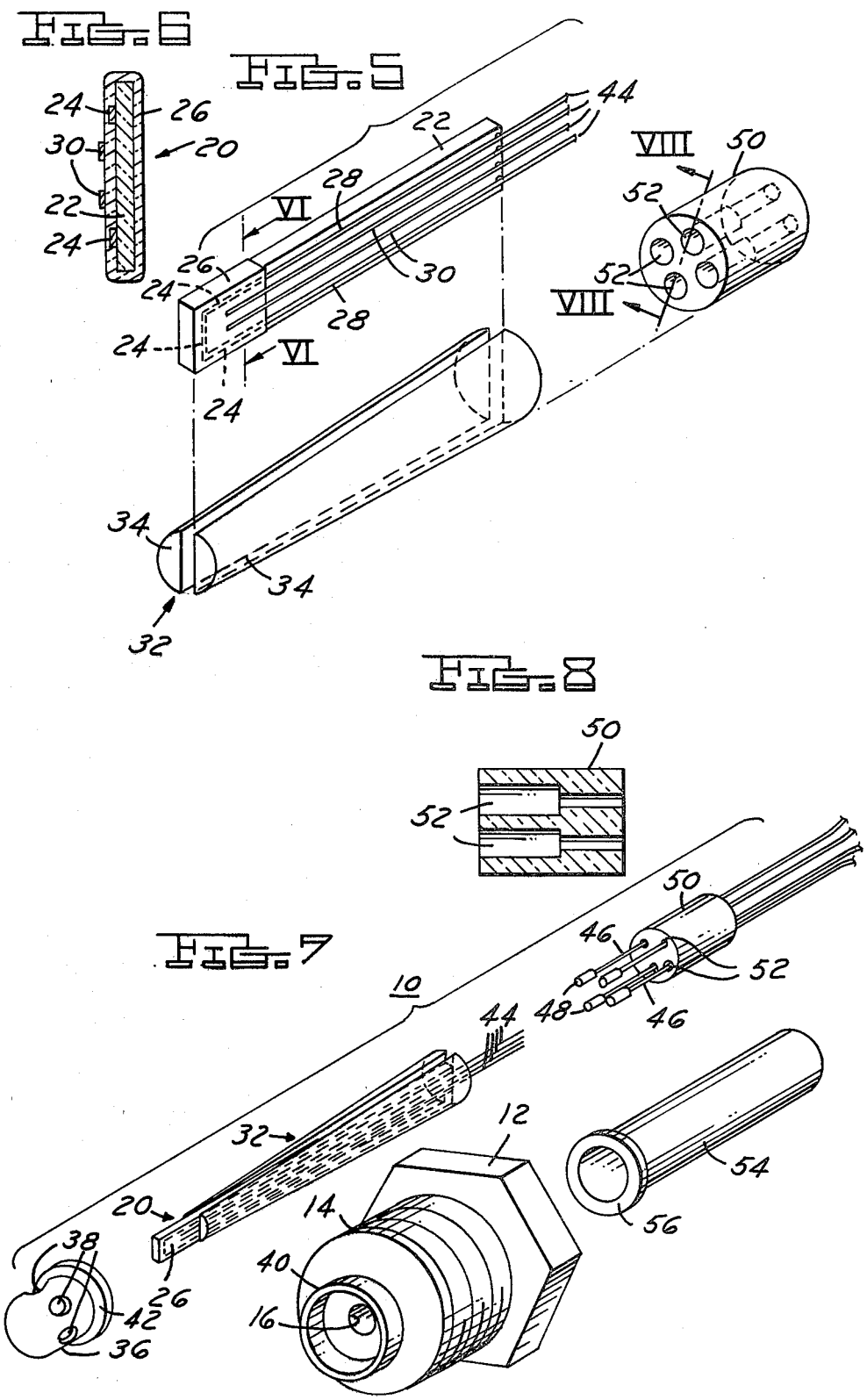

PARTIAL PRESSURE OF OXYGEN SENSOR-I

BACKGROUND ART AND PRIOR ART STATEMENT

The present invention is directed to the field of devices for controlling a hydrocarbon fuel burning device. In particular, the present invention is directed to a partial pressure of oxygen sensor which is inserted into an exhaust system which carries the exhaust gases from a hydrocarbon fuel burning device. The partial pressure of oxygen sensor is used with appropriate circuitry and mechanical devices associated therewith for controlling the amount of fuel which is introduced into the hydrocarbon fuel burning device. The amount of fuel being introduced into the device is a function of the amount of oxygen detected by the partial pressure of oxygen sensor in the exhaust gases flowing through the exhaust system.

Ceramic exhaust gas sensors of the electrically variable resistance type are known. For example, commonly assigned U.S. Pat. No. 3,893,230 by H. L. Stadler et al describes one such sensor fabricated from titania ceramic material. Also, commonly assigned U.S. Pat. No. 3,933,028 describes such a sensor fabricated from cobalt monoxide ceramic material. Each of these sensor materials demonstrates an electrical resistance change as a function of the partial pressure of oxygen in the gaseous environment of the ceramic material when that material is located in the exhaust system of a hydrocarbon fuel burning device. The resistance changes may be measured by suitable electrodes. Each of the named sensing materials functions best at an elevated temperature.

The present invention is directed to a particular structure for forming a partial pressure of oxygen sensor. The particular structure is one which provides a sensor of rugged construction, yet one which is efficient and effective in operation.

DISCLOSURE OF THE INVENTION

This invention is directed to a partial pressure of oxygen sensor and, more particularly, to a partial pressure of oxygen sensor for insertion into an exhaust system of a hydrocarbon fuel burning device.

In accordance with the teachings of this invention, the partial pressure of oxygen sensor comprises the following combination. A mounting body is formed of a metallic material. This mounting body is threaded on one end so that it may be secured to the exhaust system of the hydrocarbon fuel burning device. The mounting body has a conical configured bore extending along a central axis thereof with the smaller end of the bore located at the threaded end of the mounting body.

The combination includes an elongated heated sensing element of generally rectangular cross section which is constructed in the following manner. A ceramic support is provided, and upon a leading portion thereof there is bonded a resistance heater element. A titania dioxide sensor element is also bonded to the leading portion of the ceramic support so that the resistance heater can heat the sensor element to a required temperature when a preselected voltage is applied across the resistance heater element. A plurality of electrically conductive paths are bonded to the ceramic support. The electrically conductive paths independently connect the resistance heater element to a source of voltage and the titania dioxide sensor element to a sensing element.

The combination also includes a two-piece insulator body of ceramic material for supporting and protecting the elongated heated sensing element. Each piece of the insulator body has a shape approximating a half-cone with the smaller cross section of the half-cone being at a leading portion of the two-piece insulator body. The two-piece insulator body sandwiches the heated sensing element therebetween with a leading portion of the heated sensing element projecting beyond the leading portion of the two-piece insulator body. The two-piece insulator body sandwiching the heated sensing element therebetween is received in the conical configured bore of the mounting body in a manner such that the leading portion of the heated sensing element projects beyond the threaded end of the mounting body. A first projection tube, having an opening therein, is secured to the threaded end of the mounting body for protecting the leading portion of the heated sensing element.

The combination includes a plurality of fine electrical lead lines. One of the fine lead lines is bonded to and extends from each of the conductive paths bonded to the ceramic support. A plurality of electrical lead lines are also provided which are equal in number to the fine electrical lead lines. A plurality of crimped bands are also employed. Each of the crimped bands interconnects paired ones of the electrical lead lines and the fine electrical lead lines.

The combination also includes a second ceramic insulator body which has a plurality of passageways therein equal in number to the plurality of crimped bands. The passageways are so constructed and arranged that each of the passageways has an associated pair of the interconnected leads passing therethrough. Each of the crimped bands interconnecting the leads comes into locating engagement with the side walls defining the associated passageways in order to locate the interconnected leads positively within the passageway.

A second protection tube has one end thereof secured to an end of the mounting body not having the threads thereon. The second protection tube encloses and protects the second ceramic insulator body and the elements which are received within and pass therethrough.

A ceramic cement occupies a volume of the oxygen sensor between the second ceramic insulator body and a rear portion of the two-piece insulator body and heated sensing element sandwiched therebetween. A high temperature resistant sealant material occupies a volume between the second ceramic insulator body and a free end of the second protection tube. An electrical terminal is connected to the plurality of electrical lead lines for independently connecting the lead lines as required to a source of voltage and to a sensing circuit.

BRIEF DESCRIPTION OF THE DRAWINGS

The novel features that are considered characteristic of the invention are set forth with particularlity in the appended claims. The invention itself, however, both as to its organization and its method of operation, together with additional objects and advantages thereof will best be understood from the following description of specific embodiments when read in conjunction with the accompanying drawings, wherein like reference characters indicate like parts throughout the several figures, and in which:

FIG. 1 is an elevational view of an assembled partial pressure of oxygen sensor in accordance with the teachings of this invention;

FIG. 2 is a plan view of the oxygen sensor of FIG. 1;

FIG. 3 is an elevational view taken along line III—III of FIG. 2 showing a cross section of the oxygen sensor of this invention;

FIG. 4 is a bottom view of the sensor of FIG. 1;

FIG. 5 is a perspective view of a heated sensing element and two-piece insulator body and other elements associated therewith;

FIG. 6 is a cross section view taken along line VI—VI of FIG. 5 showing greater details of the heated sensing element;

FIG. 7 a schematic view of various elements making up the oxygen sensor of this invention prior to assembly of the structure; and FIG. 8 is a cross sectional view taken along line VIII—VIII of FIG. 5 to show greater details of the construction of a second ceramic insulator body.

BEST MODE AND INDUSTRIAL APPLICABILITY

The following description is what I consider to be a preferred embodiment of my partial pressure of oxygen sensor. The following description also sets forth what I now contemplate to be the best mode of building this oxygen sensor. This description is not intended to be a limitation upon the broader principles of this oxygen sensor, and while preferred materials are used to illustrate the oxygen sensor in accordance with the requirements of the patent laws, it does not mean that the oxygen sensor can be constructed only with the stated materials as others may be substituted therefor.

In accordance with the teachings of a preferred embodiment of this invention, a partial pressure of oxygen sensor, generally identified by the numeral 10, is shown in the drawings. The oxygen sensor is made up of a plurality of elements for forming the total combination. The plurality of elements will be described in greater detail hereinbelow. As is well known to those skilled in the art, the oxygen sensor is designed for insertion into an exhaust system of a hydrocarbon fuel burning device. The oxygen sensor serves as a device for sensing the amount of oxygen in the exhaust gases. The oxygen sensing device produces a variable voltage in response to the amount of oxygen in the ambient surrounding the same, the voltage being an indication of the partial pressure of oxygen. The resistance of the oxygen sensor is measured by associated circuitry which uses the same to set an air/fuel metering device, such as a carburetor, to obtain a desired stoichiometric relationship between the air coming into the fuel burning device and the amount of fuel being burned. All of this type of operation is well known to a skilled artisan.

A first portion of the oxygen sensor 10 is a mounting body 12. The mounting body is formed of a metallic material and has a threaded portion 14 on one end thereof. The threaded portion is used for securing the oxygen sensor to the exhaust system of the hydrocarbon fuel burning device.

As is seen only in FIG. 3, the mounting body 12 has a conical configured bore 16 extending along a central axis thereof. The conical configured bore has its smaller end at the threaded portion of the mounting body. The purpose of this bore will be explained in greater detail below.

An elongated heated sensing element, generally identified by the numeral 20, best seen in FIG. 5, forms another element of the oxygen sensor 10. As is seen in FIG. 5, the sensing element 20 includes a ceramic support 22 of generally rectangular cross section, preferably formed of alumina. A resistance heater element 24 is bonded to a leading portion of the ceramic support. The resistance heater is so constructed and arranged that when a preselected voltage is applied thereto the heater will heat the sensing element 20 to a temperature range suitable for best operation of the device to detect the partial pressure of oxygen. In the case of a titania sensor, the temperature range is 600°–650° C. The details of construction of the sensing element 20 are set forth in a commonly assigned co-pending application entitled "Method of Making a Titania Dioxide Sensor Element-I", identified by Ser. No. 429,410, filed on even date herewith.

A titania dioxide sensor element 26 is also bonded to the leading portion of the ceramic support 22 and in part overlies the resistance heater element 24. A plurality of electrically conductive paths 28-28 and 30-30 are also bonded to the ceramic support. The conductive paths 28-28 connect the resistance heater element 24 to a source of voltage, and the electrically conductive paths 30-30 connect the titania dioxide sensor element 26 to a sensing circuit in a manner which will be described in greater detail hereinbelow.

The next element of the combination is a two-piece insulator body, generally identified by the numeral 32, formed of a ceramic material. The two-piece insulator body is formed of two insulator half-bodies 34-34 having the shape approximating a half-cone with the smaller cross section of each half-cone being at a leading portion of that half-cone. As is best seen in FIG. 7, the two-piece insulator body 32 sandwiches the sensing element 20 therebetween with the leading portion of the sensing element projecting beyond the leading portion of the two-piece insulator body. The two-piece insulator body may be assembled with the sensing element by cementing them together with a ceramic cement.

As is best seen in FIG. 3, the two-piece insulator body 32, with the sensing element 20 sandwiched therebetween, is received in the conical configured bore 16 of the mounting body 12 in a manner such that the leading portion of the sensing element projects beyond the threaded portion 14 of the mounting body. A first protection tube 36 having a plurality of openings 38 therein is bonded to the lower end of the threaded portion 14 of the mounting body 12. This first portion tube protects and surrounds the leading portion of the sensing element 20. When the oxygen sensor 10 is in an installed position, the openings 38 allow exhaust gases to enter the first protection tube and surround the sensing element 20 so that a reading of the partial pressure of oxygen in those exhaust gases can be obtained. The first protection tube 36 is joined to the mounting body 12 by folding over of a lip portion 40 of the mounting body to catch a lip portion 42 of the first protection tube.

A plurality of fine electrical lead lines 44-44 are resistance welded to the electrically conductive paths 28-28 and 30-30, as is best seen in FIG. 5. As will be best understood by reference to FIGS. 3 and 7, a plurality of electrical lead lines 46-46 are also provided which are equal in number to the number of fine electrical lead lines 44-44. A plurality of crimped bands 48-48 are independently used for interconnecting paired ones of the fine electrical lead lines 44-44 and the electrical lines 46-46. Paired lead lines are inserted within the band and the crimped band 48 is then crimped in order to secure the lead lines therewithin.

A second ceramic insulator body 50 also forms part of the oxygen sensor. As is best seen in FIG. 8, the second ceramic insulator body has a plurality of stepped passageways 52-52 passing therethrough. These passageways are so constructed and arranged that each of the passageways will have an associated pair of interconnected leads passing therethrough with the crimped band interconnecting the leads coming into locating engagement with the side walls defining the passageway, as may best be seen in FIG. 3. This helps to support any load which may be placed on the wires by applying pressure to the electrical lead lines 46-46.

A second protection tube 54, best seen in FIGS. 3 and 7, has a lip portion 56 by which it is sealed by means of a lip portion 58 to an end of the mounting body 12 not having the threaded portion 14 thereon. The second protection tube 54 encloses and protects the second ceramic insulator body 50 and the elements received therein and passing therethrough.

As is seen only in FIG. 3, a ceramic cement 60 occupies a volume between the second ceramic insulator body 50 and a rear portion of the two-piece insulator body 32 and sensing element 20 sandwiched therebetween. In accordance with the assembly techniques, the second protection tube 54 is crimped by a lip portion 56 thereof to a lip portion 58 of the mounting body 12. Thereafter, the two-piece insulator body 32 with the heated sensing element 20 sandwiched therebetween is introduced through the top of the second protection tube 54. After proper seating of this two-piece insulator body and sensing element sandwiched therebetween in the conical configured bore 16 of the mounting body 12, a portion of the second protection tube is filled with the ceramic cement 60. While the cement is still wet, the second ceramic insulator body 50 is also introduced through the top of the second protection tube and forced against the ceramic cement, and the second protection tube is crimped at crimp 62 to hold the second ceramic insulator body 50 in place.

After the crimping operation, and after the ceramic cement 60 has been allowed to cure, the remainder of the second protection tube is filled with a high temperature resistant sealant material 64, seen only in FIG. 3. The high temperature sealant material occupies a volume between the second ceramic insulator body 50 and a free end of the second protection tube 54. A preferred high temperature resistant sealant material can be, for example, a silicone RTV material suitable for high temperature environments; that is, environments heated to a temperature of approximately 300° C. This sealant material will seal the top of the oxygen sensor 10 against moisture and salt spray. As is best seen in FIGS. 1 and 3, a free end 66 of the second protection tube 54 is crimped around the high temperature sealant material 64 to complete the sealing of the oxygen sensor 10. Multiple crimps may be used for sealing if desired.

The electrical lead lines 46-46 extending from the free end 66 of the second protection tube 54 may be secured to any suitable electrical connector (not shown) so that those leads may be properly connected to required circuitry. For example, the electrical leads 46-46 associated with the resistance heater element 24 will be connected to a source of voltage so that the heating circuit can be actuated to heat the oxygen sensor 10. In a similar manner, the electrical lead lines 46-46 associated with the titania dioxide sensor element 26 should be connected by means of the suitable connector to a sensing circuit. In this manner the output of the titania dioxide sensor element may be applied to suitable circuitry, whereby other mechanical portions of the hydrocarbon fuel burning device may be controlled so that the proper amount of oxygen is employed with the fuel being burned in the system. If desired, the resistance heater element may be used as a voltage divider to supply the reference voltage to the titania dioxide sensor element.

While a preferred embodiment of the invention has been illustrated and described, it will be obvious to those skilled in the art that various changes and modifications may be made without departing from the invention, and it is intended to cover in the appended claims all such modifications and equivalents as fall within the true spirit and scope of this invention.

I claim:

1. A partial pressure of oxygen sensor for insertion into an exhaust system of a hydrocarbon fuel burning device, comprising in combination:

a mounting body formed of a metallic material threaded on one end for securement to the exhaust system and having a conical configured bore extending along a central axis thereof, said conical configured bore having its smaller end at said threaded end of said mounting body;

an elongated heated sensing element of generally rectangular cross section including: a ceramic support, a resistance heater element bonded to a leading portion of said ceramic support, a titania dioxide sensor element also bonded to said leading portion of said ceramic support so that said resistance heater heats said sensor element to a required temperature when a preselected voltage is applied across said resistance heater element, a plurality of electrically conductive paths bonded to said ceramic support, said paths for independently connecting said resistance heater element to a source of voltage and said titania dioxide sensor element to a sensing circuit;

a two-piece insulator body of ceramic material, each piece of said insulator body having a shape approximating a half-cone with the smaller cross section of said half-cone being at a leading portion of said two-piece insulator body, said two-piece insulator body sandwiching said heated sensing element therebetween with said leading portion of said heated sensing element projecting beyond said leading portion of said two-piece insulator body, said two-piece insulator body sandwiching said heated sensing element therebetween being received in said conical configured bore of said mounting body in a manner such that said leading portion of said heated sensing element projects beyond said threaded end of said mounting body;

a first protection tube means secured to said threaded end of said mounting body for protecting said leading portion of said heated sensing element, said first protection tube having an opening therein through which exhaust gases may flow into contact with said heated sensing element;

a plurality of fine electrical lead lines, one of said fine lead lines being bonded to and extending from each of said conductive paths bonded to said ceramic support;

a plurality of electrical lead lines equal in number to said fine electrical lead lines;

a plurality of crimped bands, each of said crimped bands interconnecting paired ones of said electrical lead lines and said fine electrical lead lines;

a second ceramic insulator body having a plurality of passageways therein equal in number to said plurality of crimped bands, said passageways being so constructed and arranged that each of said passageways has an associated pair of said interconnected leads passing therethrough with said clipped band interconnecting the same coming into locating engagement with the side walls defining said associated passageway;

a second protection tube means having one end secured to an end of said mounting body not having said threads thereon for enclosing and protecting said second ceramic insulator body and elements received therein and passing therethrough;

a ceramic cement occupying a volume between said second ceramic insulator body and a rear portion of said two-piece insulator body and heated sensing element sandwiched therebetween;

a high temperature resistant sealant material occupying a volume between said second ceramic insulator body and a free end of said second protection tube means; and electrical terminal means connected to said plurality of electrical lead lines for independently connecting said lead lines as required to a source of voltage and to a sensing circuit.

2. The partial pressure of oxygen sensor as defined in claim 1, wherein each of said passageways of said second ceramic insulator body are of a stepped design in which a first portion of each passageway has a diameter greater than an associated one of said crimped bands received therein, and a second portion of each passageway has a diameter less than an associated one of said crimped bands but greater than an associated one of said electrical lead lines passing therethrough.

3. The partial pressure of oxygen sensor as defined in claim 1 or claim 2, wherein said first protection tube has a plurality of openings therein.

* * * * *